United States Patent [19]

Robertson et al.

[11] Patent Number: 5,190,728

[45] Date of Patent: Mar. 2, 1993

[54] APPARATUS FOR MONITORING FOULING IN COMMERCIAL WATERS

[75] Inventors: Linda R. Robertson, St. Charles; Jeffrey R. Cantrall, Naperville, both of Ill.

[73] Assignee: Nalco Chemical Company, Naperville, Ill.

[21] Appl. No.: 781,078

[22] Filed: Oct. 21, 1991

[51] Int. Cl.$^5$ .......................................... G01N 31/12
[52] U.S. Cl. ................................... 422/68.1; 422/79; 422/62; 436/62; 436/52; 435/291; 204/403
[58] Field of Search ................... 422/79, 62, 88, 68.1, 422/119; 436/62, 138, 127, 52; 435/31, 34, 291, 817, 284, 285, 286; 204/153.12, 153.17, 415, 403

[56] References Cited

U.S. PATENT DOCUMENTS

| | | | |
|---|---|---|---|
| 3,731,522 | 5/1973 | Mikesell | 436/62 |
| 4,350,763 | 9/1982 | Suzuki et al. | 435/291 |
| 4,517,053 | 5/1985 | Devine | 422/62 |
| 4,579,642 | 4/1986 | Niiyama et al. | 204/403 |
| 4,833,089 | 5/1989 | Kojima et al. | 435/284 |
| 5,085,759 | 2/1992 | Karker | 204/415 |

FOREIGN PATENT DOCUMENTS 5892951 11/1981 Japan .

OTHER PUBLICATIONS

K. Riedel, et al., "A Microbial Sensor For BOD", *Wat. Res.*, vol. 24, No. 7, pp. 883-887 (1990).

I. Karube, et al., "A Rapid Method for Estimation of BOD by Using Immobilized Microbial Cells", U. Ferment. Technol. vol. 55, pp. 243-248 (1977).

*Primary Examiner*—James C. Housel
*Assistant Examiner*—Lien Tran
*Attorney, Agent, or Firm*—Lloyd L. Zickert

[57] ABSTRACT

A fouling monitor and method for sensing fouling in commercial waters and for differentiating between microbiological fouling and chemical fouling, which includes a dissolved oxygen probe disposed in a slip stream of water and means for providing an abundance of oxygen and nutrient to the microbial activity whereby a decrease in dissolved oxygen level is sensed due to the increased respiration of the microbes when microbiological fouling occurs. A polyester screen is mounted over the sensing end of the dissolved oxygen probe to promote microbiological fouling by providing a means for engaging the microbes and to enhance differentiation between the biological component and the non-viable/chemical component.

14 Claims, 2 Drawing Sheets ial fouling in processed waters has not been possible.

APPARATUS FOR MONITORING FOULING IN COMMERCIAL WATERS

This invention relates in general to a fouling monitor for detecting fouling in commercial or process waters, and more particularly to a fouling monitor for differentiation of biological deposits from other deposits, and still more particularly to a method of detecting biological fouling in commercial waters from non-viable/chemical fouling, and still more particularly to a fouling monitor for continuously measuring fouling deposits to determine how to better treat a commercial or process water.

BACKGROUND OF THE INVENTION

Commercial waters, such as those used in paper systems, cooling systems, mining systems, and metal systems, are susceptible to contamination and fouling. In order to control such fouling, such waters have been chemically treated generally by trial-and-error methodology. Either too much or too little chemical is used, which is unsatisfactory. Such fouling may be of the biological type or of the non-viable/chemical type. With respect to biological fouling, when it reaches a certain level, it becomes necessary to shut down the system for maintenance.

For example, in a paper system, when microbiological fouling in a white water reaches a certain biological level, it results in making rejectable paper that is costly to paper production. More specifically, the sessile portion of microbial activity causes deposits which are difficult to monitor. When sloughing of the deposits occurs in a paper machine, runability of the machine is affected by increased sheet defects and even paper breaks. At that time the system must be shut down for maintenance, resulting in downtime which interrupts production. It must be cleaned or "boiled out" before the system can be placed back in operation to make acceptable paper. With regard to controlling biological fouling, biocides are added to the water to kill the bacteria or microbes.

Current systems for measuring fouling lack sensitivity, require excessive maintenance, and are not automated. The only method now for differentiating between bacteriological fouling and chemical fouling is through use of destructive testing which measures "sliminess" subjectively, plate counts on a defined portion of the population, or microbial activity.

Dissolved oxygen (DO) probes have been suggested for detecting microbial activity since it is known that high levels of bacteria in fluids decrease dissolved oxygen levels. However, they are limited due to chemical fouling which gradually reduces the efficacy to measure accurate DO levels.

Further, DO probes have been used to measure microbial activity in solutions. Where the dissolved oxygen drops, it is assumed that microbial growth is occurring and the system is contaminated. However, dissolved oxygen can drop due to changes in air supply, probe-surface fouling, temperature variation, or a number of factors, thereby rendering the use of the DO probes unreliable. Thus, reliable measurement of microbiological fouling in processed waters has not been possible.

SUMMARY OF THE INVENTION

The present invention obviates prior problems in measuring microbial activity in commercial fluids, and relates to a method and apparatus for monitoring biological fouling in paper or other fluid systems so as to not only be able to optimize biocide treatment of the commercial fluid but also to better predict when maintenance is needed to regenerate the system.

The invention relates to a fouling monitor which differentiates between non-viable/chemical fouling and biological fouling and comprises the use of a dissolved oxygen probe or sensor disposed in a slip stream of the commercial water system. The commercial water is continuously supplied with a source of oxygen. As the probe gradually fouls, due to either chemical or biological fouling, the DO that is measured will be reduced. By the addition of a nutrient, a lack of further decrease in DO indicates the fouling is chemical. Further decrease in DO pursuant to the addition of nutrient indicates microbiological fouling.

The DO probe preferably includes a roughened surface onto which the microbes can cling at the sensing end of the probe so as to promote fouling and enhance the sensitivity of the probe. One form of providing a roughened surface on the sensing end of the DO probe would be to apply a mesh fabric, such as a polyester screen over the sensing end, having a suitable mesh count or size.

The level of oxygen supplied is not limited and would be such as to exceed the need of the microbes, thereby saturating the stream with oxygen. Similarly, the level of nutrient supplied would be in abundance of the needs of the microbes, and the supply levels of oxygen and nutrients would be substantially constant. Further, the temperature of the mixture of the commercial water slip stream, the oxygen and the nutrient would be maintained substantially constant. As the probe fouls, due to either chemical or biological fouling, the DO that is measured will be reduced. If the incoming stream is closed down, while still supplying oxygen, a nutrient can be introduced. If the fouling is of a chemical nature, the DO reading will be substantially unchanged. If the fouling is microbial in nature, the DO level will decrease due to increased respiration by the microbial population when nutrient is introduced. By measuring both levels, the amount of chemical and/or biological fouling can be measured.

A readout device, such as a chart recorder, would be connected to the DO probe for providing a visual indication of the dissolved oxygen level detected.

It is therefore an object of the present invention to provide a fouling monitor for continually detecting the chemical and/or biological fouling of a commercial water.

Another object of the present invention is in the provision of a system for detecting biological fouling that includes the addition of an abundance of oxygen and nutrient into the water stream being tested in the presence of a DO probe.

A further object of the invention is in the method of monitoring biological fouling in a commercial water so as to optimize the usage of biocides and other deposit control agents and to make the system in which the commercial water is used more efficient and to better predict when to shut down the system for maintenance.

Other objects, features and advantages of the invention will be apparent from the following detailed disclosure, taken in conjunction with the accompanying sheets of drawings, wherein like reference numerals refer to like parts.

DESCRIPTION OF THE INVENTION

Figure 1:
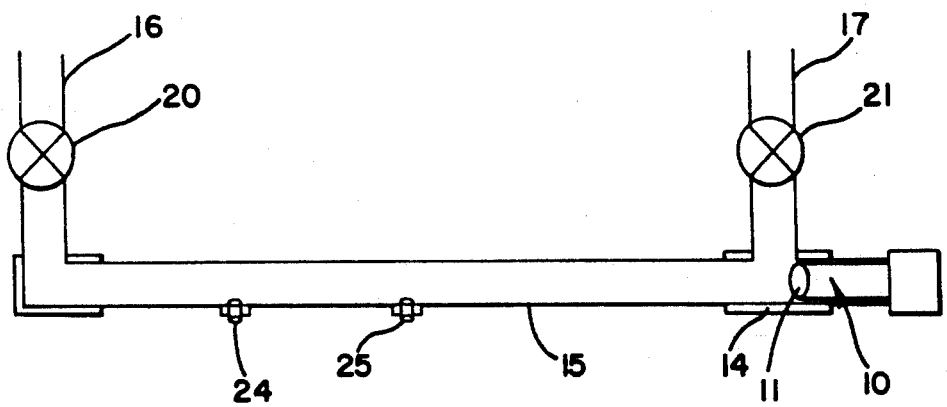
FIG. 1 is a schematic view of the apparatus for monitoring fouling according to the invention.

The method and apparatus of the invention continuously monitors the fouling level in a commercial water whereby the efficient addition of biocides to kill bacteria or microbes can be accomplished. Moreover, the apparatus and method differentiates between chemical and microbiological fouling. It is particularly important to control biological fouling in the white water of paper systems in order to avoid unsatisfactory paper-making results. In addition to monitoring biological fouling in paper systems, it is important to monitor biological fouling in cooling waters, process waters in the mining industry, and process waters in the metal industry. The present invention may be used wherever there is a need to monitor and control biological fouling in a commercial water.

The invention involves conditioning the commercial water and measuring the dissolved oxygen level preferably with a galvanic membrane type dissolved oxygen sensor or probe. One specific example of a dissolved oxygen sensor that could be used is the galvanic membrane style Model 6710/5340 made by Great Lakes Instruments. This particular sensor also includes a Mackereth electrode. Such a sensor measures electric current between electrodes which is proportional to the dissolved oxygen in the process. The sensor or probe includes electrodes, electrolyte around the electrodes, and a gas permeable membrane that functions to keep the electrolyte around the electrodes while allowing the dissolved oxygen to diffuse into the measurement chamber where the electrodes are located.

A chart recorder of a well known type is connected to the output of the probe or sensor and calibrated to record continuously the dissolved oxygen measured by the probe. The chart speed is timed so that the dissolved oxygen is measured on the chart. The dissolved oxygen level is directly related to the level of fouling.

A slip stream or side stream of the water or fluid is taken from the system for purposes of making the fouling measurements. This stream is continuously supplied with a source of air, selectively supplied with a source of nutrient, and the air and nutrient is mixed in the slip stream whereby the resulting mixture is then subjected to the dissolved oxygen probe for measurement. The air is delivered to the slip stream at a constant rate as is the nutrient when it is delivered to the slip stream. The mixture is maintained at a constant temperature during the measuring process. If the mixture is not maintained at a constant temperature, the measurement must be temperature compensated. When the nutrient is added to the slip stream, the influent is closed. From a clean state, the DO surface slowly becomes fouled, and as it becomes fouled, the recorded dissolved oxygen is reduced. Addition of the nutrient to a biologically fouled surface further reduces the dissolved oxygen and thereby provides the ability to differentiate between chemical fouling and biological fouling as the nutrient is eaten by the microbes or bacteria to further reduce the dissolved oxygen level.

The air and nutrient supplies are delivered in excess of the needs of the microbes so as to provide the most accurate measurement of the biological fouling. The nutrient may be any suitable type of sugar, such as dextrose, glutamic acid, sucrose, fructose, or any other suitable material that has a biochemical oxygen demand. It may be in the form of dry granules or it may be liquid such as a nutrient broth. The amount added is a low level and in the range of 0.05 to 0.1 grams per 600 milliliters volume. The 0.1 gram level is considered to be adequate in that it will clearly oversaturate the nutrient level.

Referring now to the drawings, and particularly to FIG. 1, the embodiment of the invention is shown by a schematic drawing which includes a dissolved oxygen probe 10 having a sensing head 11 and being of a type referred to above, or of any suitable membrane type. The probe is mounted so that the head is exposed at one end of a tee 14 associated with an intake pipe 15. The intake pipe includes an inlet 16 and an outlet 17. The inlet would be connected to the system and would take a slip stream or a side stream from the system, and the outlet could also be connected as a return to the system or to sewer.

At the inlet 16 a ball valve 20 is provided to control the opening and closing of the inlet, while at the outlet a ball valve 21 is provided to control the opening and closing of the outlet. The ball valves may be utilized for purposes of maintenance of the dissolved oxygen probe and other parts of the monitoring unit. An air supply port 24 is provided for feeding air to the pipe 15 at a constant rate. A nutrient port 25 is provided to supply nutrient to the pipe at a constant rate. When only supplying air through the air supply port, fouling will be detected when the dissolved oxygen level decreases. When nutrient is supplied through the nutrient port 25, the influent to the slip stream in the pipe 15 is closed, and in this case, it can be closed by the ball valve 20. If fouling is slowly caused by chemical activity, the dissolved oxygen level will not change when the nutrient is supplied. However, if the dissolved oxygen level decreases once the nutrient is supplied, then it can be determined that there was biological fouling in the system. The level of fouling is directly related to the level of the dissolved oxygen detected by the probe. It will be understood that suitable recording means will be connected to the dissolved oxygen probe 10 in order to read out the dissolved oxygen levels at the probe head.

Figure 2:
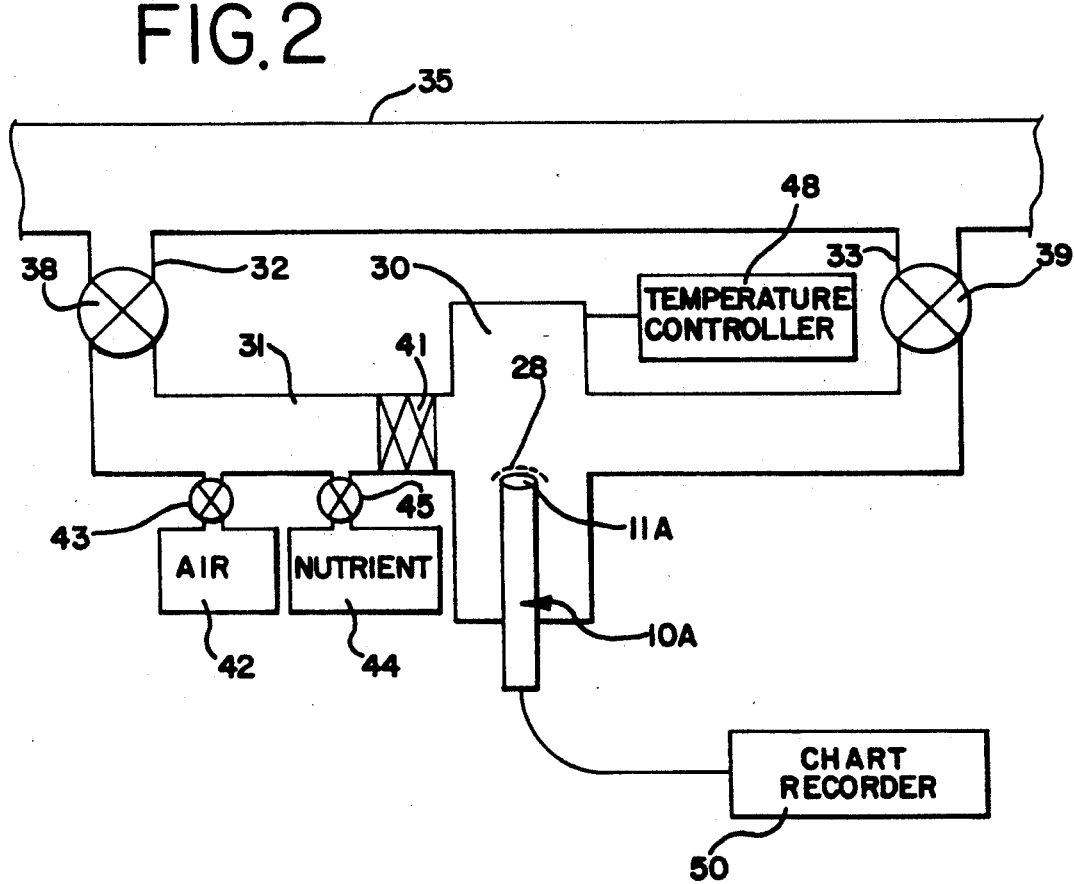
FIG. 2 is a modification of the apparatus for measuring fouling according to the invention.

Another embodiment of the invention is illustrated in the schematic diagram of FIG. 2 that differs primarily in that the probe head is provided with a roughened surface by way of covering the head with a polyester mesh fabric to enhance sensitivity and also by providing a vehicle to which the microbes can cling or attach during fouling of the probe. The polyester mesh fabric is indicated by the numeral 28 and has a mesh size of about 120×200 micrometers. It may be appreciated that other fabrics or materials of inert material having other mesh sizes could be used depending upon the nature of the commercial water and the fouling to be encountered.

The probe in this embodiment is designated by the numeral 10A having a head 11A and which is mounted in a reaction chamber 30. The reaction chamber 30 is formed in a side or slip stream pipe 31 having an inlet 32 and an outlet 33. The inlet is connected to the main stream and conduit 35 of the system for which fouling is to be measured. As above explained, the system may be, for example, a white water source to a paper-making machine, where it is important to control biological fouling in order to make quality paper.

A ball valve 38 is provided at the inlet 32, while a ball valve 39 is provided at the outlet 33, the purpose of which can be for rendering maintenance to the fouling monitor. Further, the ball valve 38 may be used to close off the influent to the probe when nutrient is to be added for the purpose of measuring or detecting biological fouling.

A mixing device 41 is provided ahead of the reaction or measuring chamber 30 in order to assure proper mixing of the air and/or nutrient in the water being carried by the slip stream. An air supply 42 is connected to the pipe 31 ahead of the mixer 41 and provided with a valve 43 which may be used to control the level of air supply. Between the air supply 42 and the mixing device 41, a nutrient supply 44 is provided which can supply nutrient to the slip stream, and a valve 45 controls the supply of nutrient. It is important that the air supply be constant and that it be at a level that exceeds the needs of the microbes or bacteria in the slip stream. Similarly, when the nutrient supply is provided to the slip stream, it is important that it be maintained at a constant level and at a level that exceeds the needs of the microbes or bacteria.

A temperature controller 48 is provided for the reaction chamber in order to maintain the temperature of the reaction chamber substantially constant, as variations in temperature affect the measurement taken by the dissolved oxygen probe 10A. Alternatively, means could be provided to compensate for slight temperature variations.

In order to read out the output of the dissolved oxygen probe 10A, a chart recorder 50 responds to the output current of the probe. Any other suitable device may be used in place of the chart recorder to monitor the dissolved oxygen probe. A record of the output of the probe can be maintained on a daily basis. Also to be noted by the chart recorder will be whether microbiological fouling exists when the nutrient is added to the slip stream.

The polyester screen covering the head of the dissolved oxygen probe accelerates fouling by providing a rough surface and places to which the microbes or bacteria can cling. It should be appreciated that in some systems it may not be necessary to provide the polyester screen covering the head of the probe, depending upon the type of fouling encountered. With respect to the probe, since it is of a membrane type, it includes probe contacts within the head in an electrolyte. The membrane holds the electrolyte but is gas-permeable to allow detection of the dissolved oxygen level. When the polyester mesh fabric is placed over the probe, it indicates a drop in oxygen by the probe, and thereafter where biological fouling is present, the addition of a nutrient will cause a further drop in the dissolved oxygen level. In the event no biological fouling is present, the addition of the nutrient will not affect the response of the probe, and therefore the fouling will have been indicated to be of the non-viable chemical type.

Figure 3:
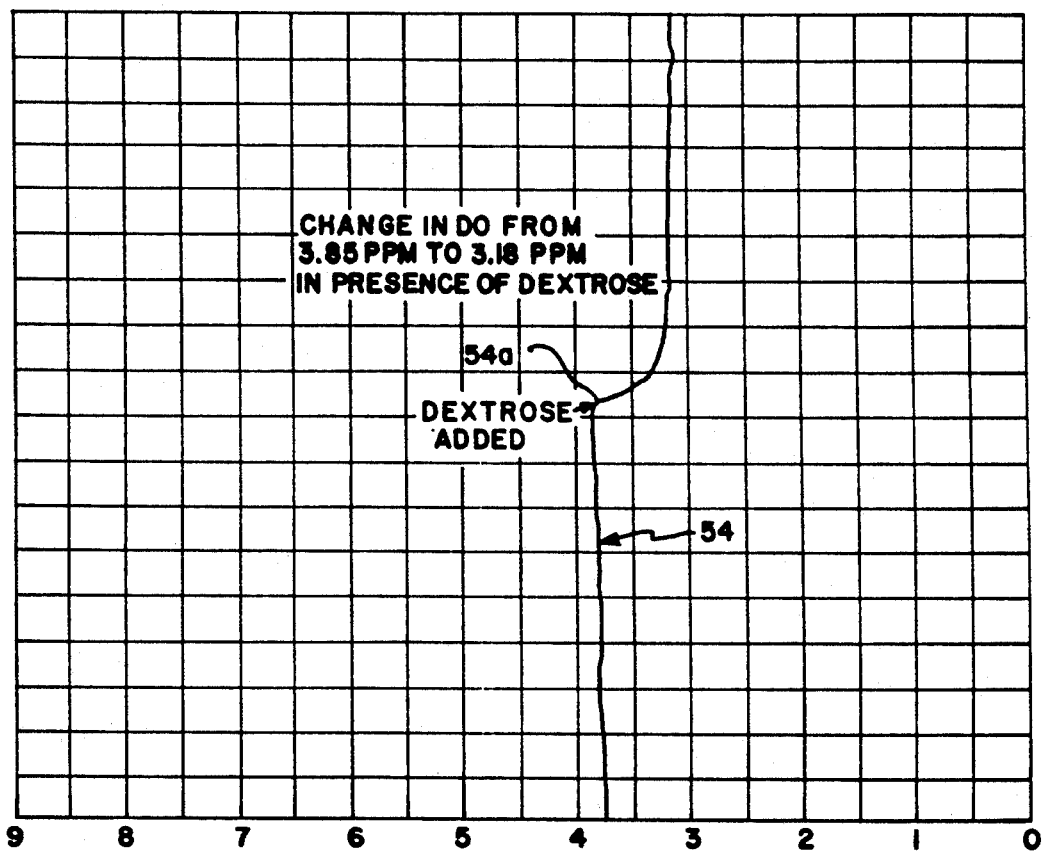
FIG. 3 is a run chart of a fouled dissolved oxygen probe in a phosphate buffer showing increased respiration/lower dissolved oxygen levels when dextrose has been added to the system.

The operation of a laboratory setup of the invention is reflected in the run chart shown in FIG. 3, which was taken from a chart recorder. The setup included covering the dissolved oxygen probe with a polyester cloth and allowing it to foul in a high carbohydrate, low protein, nutrient solution. The probe was disposed in a jacketed vessel heated by a circulator heater to maintain the temperature constant at 40° C. Air was supplied by an air diffuser and a magnetic stir bar was set at a constant rate to provide mixing of the solution. The dissolved oxygen levels measured by the probe decreased as surface fouling of the probe increased. The solution was a phosphate buffer and the chart produced the recorded line 54. At a given point, dextrose was added to the solution, the point being indicated by the numeral 54a, where it may be noted that the dissolved oxygen level immediately dropped from 3.85 ppm to 3.18 ppm. Thus, when the dextrose was added to the solution, it showed increased respiration and a lower dissolved oxygen level.

Figure 4:
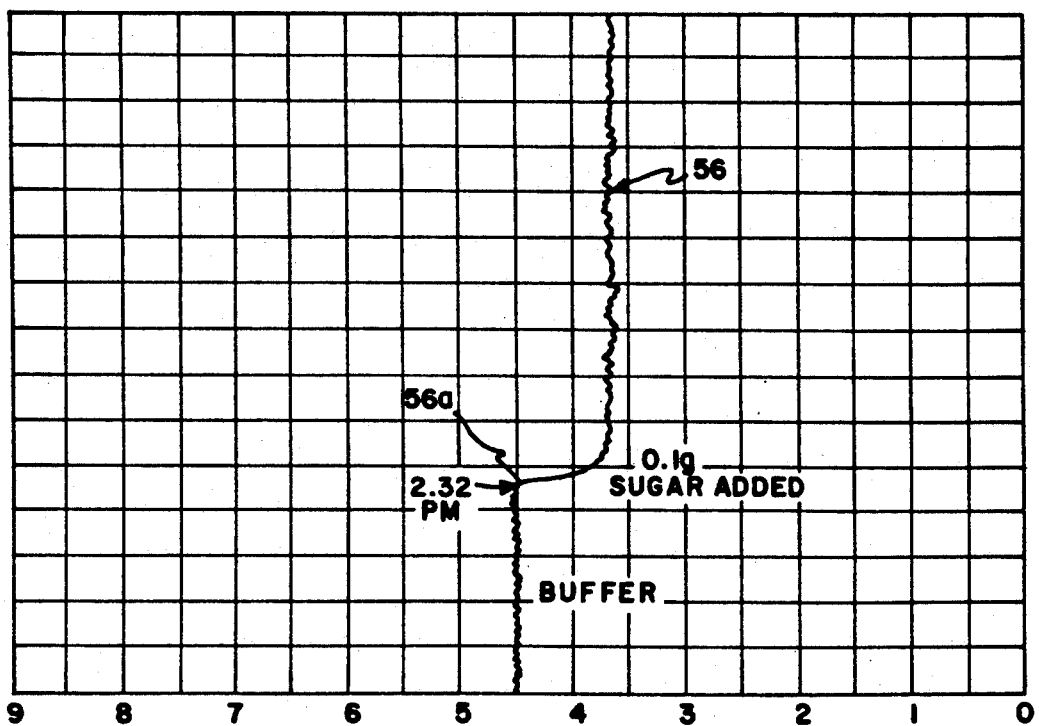
FIG. 4 is a run chart of a fouled dissolved oxygen probe in a phosphate buffer showing increased respiration/lower dissolved oxygen levels when dextrose and nutrient broth is added to the solution.

Another laboratory setup and the recording of the dissolved oxygen levels is shown in FIG. 4 where the recording line is indicated by the numeral 56. The addition of 0.1 gram of dextrose and one milliliter of nutrient broth to the fouling sensor in a buffer solution showed a drop in dissolved oxygen level from 4.5 ppm to 3.7 ppm in five minutes. The addition of the dextrose was made at point 56a. The chart speed used here was 12 centimeters per hour, or one centimeter every five minutes.

In view of the foregoing, it will be appreciated that the present invention is capable of monitoring fouling in a commercial water and differentiating between chemical and biological fouling so as to allow the efficient addition of biocides in order to control biological fouling.

It will be understood that modifications and variations may be effected without departing from the scope of the novel concepts of the present invention, but it is understood that this application is to be limited only by the scope of the appended claims.

The invention is hereby claimed as follows:

1. An apparatus for monitoring biological fouling in commercial water by taking a sample from the main stream of a process, which device comprises means for maintaining the sample at a substantially constant temperature, means for continuously supplying oxygen to the sample, means for selectively supplying nutrient to the sample, means for detecting the dissolved oxygen level, said detecting means including a dissolved oxygen probe having a sensing head with a roughened surface for enhancing the attachment of fouling material, and means connected to the detecting means for recording the dissolved oxygen level.

2. The apparatus of claim 1, wherein said means for supplying oxygen includes an air supply.

3. The apparatus of claim 2, wherein the means for recording includes a chart recorder.

4. A fouling monitor for continuously measuring chemical and biological fouling in a commercial water system having a main stream of the water, wherein the biological and chemical fouling is due to the process of fouling deposits, said monitor comprising means for taking a slip stream of water from the main stream of the water, a dissolved oxygen probe for measuring dissolved oxygen levels, said probe having a sensing head, said sensing head having a roughened surface for enhancing the attachment of fouling deposits, means for continuously supplying air to the slip stream, means for selectively supplying nutrient to the slip stream, means for mixing the air and nutrient in the slip stream, a chamber in which the sensing head of the dissolved oxygen probe is received to expose the head to the slip stream mixture, and means for recording the output of the probe, whereby the probe continuously measures fouling, and the addition of nutrient differentiates between chemical and biological fouling.

5. The fouling monitor of claim 4, which further comprises means for selectively closing off the influent to the slip stream.

6. The fouling monitor of claim 5, which further comprises means for maintaining the supply of air substantially constant and in excess of the needs of the fouling deposits in the slip stream and on the sensing head.

7. The fouling monitor of claim 5, which further comprises means for maintaining the supply of air and nutrient when supplied substantially constant and in excess of the needs of the fouling deposits in the slip stream.

8. The fouling monitor of claim 7, which further includes means for maintaining the temperature of the mixture substantially constant.

9. The fouling monitor of claim 7, which further includes means compensating for slight temperature variation.

10. The fouling monitor of claim 8, wherein the recording means includes a chart recorder.

11. The fouling monitor of claim 4, wherein said roughened surface means includes a mesh fabric.

12. The fouling monitor of claim 4, wherein said roughened surface means includes a polyester mesh fabric.

13. The fouling monitor of claim 11, wherein the fabric has a mesh size of 120×200 micrometers.

14. The fouling monitor of claim 12, wherein the fabric has a mesh size of 120×200 micrometers.

* * * * *